United States Patent
Shabanov et al.

(10) Patent No.: US 7,393,981 B2
(45) Date of Patent: Jul. 1, 2008

(54) METHOD OF PREPARATION OF METHYL-BENZYL-KETONE

(75) Inventors: Alimamed Latif Shabanov, Baku (AZ); Elmira Mamedem Ramazanova, Baku (AZ)

(73) Assignee: Property Development Corporation International, Ltd, Inc., Baku, AZ (US)

( * ) Notice: Subject to any disclaimer, the term of this patent is extended or adjusted under 35 U.S.C. 154(b) by 0 days.

(21) Appl. No.: 12/001,957

(22) Filed: Dec. 12, 2007

(65) Prior Publication Data

US 2008/0097128 A1    Apr. 24, 2008

Related U.S. Application Data

(62) Division of application No. 11/177,893, filed on Jul. 8, 2005, now abandoned.

(51) Int. Cl.
*C07C 45/65*    (2006.01)
*C07C 45/72*    (2006.01)
(52) U.S. Cl. .................................................... 568/319
(58) Field of Classification Search .................. 568/319
See application file for complete search history.

(56) References Cited

U.S. PATENT DOCUMENTS 2,891,095 A * 6/1959 Opitz et al. .................. 568/406
4,754,074 A * 6/1988 Hussmann ................... 568/319

OTHER PUBLICATIONS

Herbst et al. "Methyl Benzyl Ketone", http://www.orgsyn.org, Oct. 3, 2004.*
Mastermind, "Phenyl-2-propanone (P2P) from Phenylacetic Acid and Acetic Acid" (Tube Furnace Method),☐☐http://www.dimethyltryptamine.net/chemistry/tubefurnace.html, Oct. 3, 2004.*
Kazansky et al. (Eds.), "Reactions and Methods for Investigating Organic Compounds", Book 13, Khimiya Publishers, Moscow, 1964.*
Tamtsyura et al. "Methods for Synthesizing Chemical Reagents and Compounds", Learned Papers, Issue 25, IREA, Moscow, 1974.*

* cited by examiner

*Primary Examiner*—Sikarl A Witherspoon
(74) *Attorney, Agent, or Firm*—James J. Murphy; Thompson & Knight, LLP

(57) ABSTRACT

A catalytic process for producing ketones and particularly methyl-benzyl-ketone is provided. A catalyst comprising thorium oxide and a second metal oxide, preferably MnO, is formed on a substrate, preferably pumice. Phenylacetic acid and acetic acid are reacted in the presence of the catalyst to form methyl-benzyl-ketone.

10 Claims, 1 Drawing Sheet

METHOD OF PREPARATION OF METHYL-BENZYL-KETONE

CROSS-REFERENCE TO RELATED APPLICATION

The present application is a divisional of U.S. patent application Ser. No. 11/177,893, filed Jul. 8, 2005 now abandoned.

BACKGROUND OF THE INVENTION

1. Field of the Invention

The present invention relates generally to a catalyst and catalytic method for preparing ketones from carboxylic acids and in particular to a catalyst and catalytic method for preparing methyl-benzyl-ketone (MBK).

2. Description of Related Art

It is known that carboxylic acids can be used as precursors for the production of ketones. See e.g., John W. Nicholson, Alan D. Wilson, "The Conversion of Carboxylic Acids to Ketones: A Repeated Discovery," J. Chem. Educ. 81, 1362 (2004); B. A. Bolotov et al., "Practical Operations in Organic Catalysis," 143-145 (University of Leningrad Press) (1959) (Russian); K. Veigand, "Experimental Methods in Organic Chemistry," 484-490 (D. N. Vitkovsky et al. trans., V.N. Velov ed., Foreign Literature Publishers, Moscow, 1953) (Russian). Current processes for the production of ketones from carboxylic acids, such as those processes disclosed in Nicholson, Bolotov, and Veigand using a single-metal metal-oxide catalyst, are generally slow and provide relatively low yields of the desired ketone. In addition, the single-metal metal-oxide catalysts used in current processes tend to lose their catalytic activity after each process cycle and must be replenished. These issues make it difficult for current processes to be used as continuous processes that are commercially viable.

These issues are particularly evident in the current processes for the production of MBK from carboxylic acids. Current processes for the production of MBK are slow, and generally the yield of MBK by known methods tends to be less than 65%. One of the reasons that known methods of MBK production do not give a high yield of MBK production is because di-benzyl-ketone is formed as a by-product substance, which requires additional refinement. The production of di-benzyl-ketone occurs naturally and can reduce the yield of MBK in the current processes to 55% or less. In addition to yield problems, the catalysts used in current methods loose their activity after each cycle of the process and must be replenished. These disadvantages thus make it difficult to use current processes for commercially viable, continuous process MBK production.

A need exists, therefore, for a high-yield catalytic process for producing ketones, particularly MBK from carboxylic acids. A need also exists for a catalyst that does not need to be regenerated or replenished after each production cycle.

BRIEF SUMMARY OF THE INVENTION

The problems present in the known methods for producing ketones are solved by the systems and methods of the principles of the present invention. The principles of the present invention make possible the manufacture of ketones, particularly MBK, through a continuous, commercially-viable, high-yield process. The principles of the present invention allow the production of MBK with a yield potential of around 70% or greater by causing a sharp decrease in the formation of by-products, specifically di-benzyl-ketone, and by preventing catalyst activity loss. This is important because ketones, particularly MBK, have great potential in the synthesis of important organic substances and medicines.

In accordance with the principles of the present invention, an inorganic polymer catalyst comprising thorium oxide and a second metal oxid and a method for preparing same is described. This inorganic polymer catalyst is useful in the preparation of ketones from carboxylic acids, particularly in the preparation of MBK from acetic and phenylacetic acids.

In further accordance with the principles of the present invention, carboxylic acids are reacted in the presence of the described inorganic polymer catalyst to form ketones. In the case of the reaction of acetic and phenylacetic acids, the acetic and phenylacetic acids are decomposed in a reactor containing a $ThO_2$ and $MnO$ catalyst sewn to a substrate, such as pumice, to form MBK. One of the benefits of the invention is that it provides an improved catalytic method of MBK preparation that allows manufacture MBK through a continuous, commercially-viable, high-yield process. A further benefit of the invention is a sharp decrease in the formation of the byproduct, di-benzyl-ketone. A further benefit of the principles of the present invention is prevention of catalyst activity loss. The catalyst described as part of the present invention has catalytic activity that can last for up to and over two years. An additional benefit of the principles of the present invention over known processes is that the invented catalyst also provides regulated selectivity of MBK formation during the process.

Other objects, features, and advantages of the principles of the present invention will become apparent with reference to the drawings and detailed description that follow.

BRIEF DESCRIPTION OF THE DRAWINGS

For a more complete understanding of the principles of the present invention, and the advantages thereof, reference is now made to the following descriptions taken in conjunction with the accompanying drawings, in which.

DETAILED DESCRIPTION OF THE PREFERRED EMBODIMENT

Figure 1:
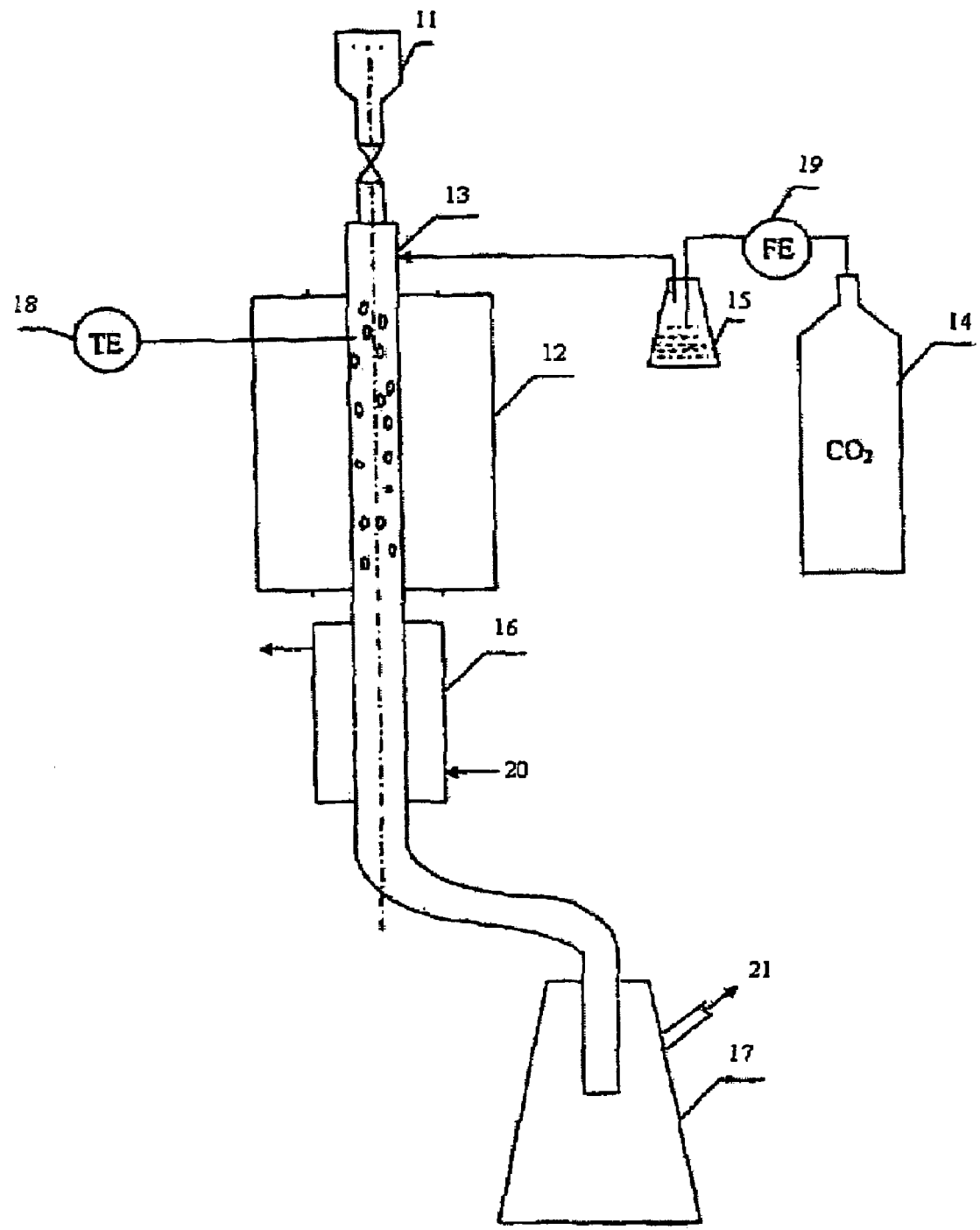
FIG. 1 is a schematic flow diagram illustrating an exemplary process embodying the principles of the present invention.

In the following detailed description of specific embodiments, reference is made to the accompanying drawing which forms a part hereof, and in which is shown by way of illustration specific embodiments in which the principles of the present invention may be practiced.

The principles of the present invention concern the preparation of an inorganic polymer catalyst useful for preparing ketones, particularly MBK, and the process for producing ketones, particularly MBK, using the prepared catalyst. The principles of the present invention result in high product yield, e.g. greater than 70% for MBK, and also conserves catalyst, resulting in a continuous, commercially-viable ketone manufacturing process.

The preparation of ketones from carboxylic acids proceeds by the following general reaction where R1 and R2 represent alkyl and/or aryl groups:

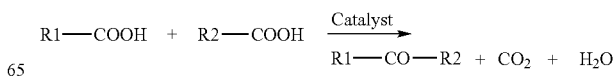

If R1 and R2 represent different functional groups, this reaction can produce three different ketones: two symmetrical ketones that are generally undesirable byproducts and one asymmetrical ketone that is the desired reaction product. The greater the molecular weight difference between the two reaction precursor carboxylic acids, the easier it is to separate the reaction products. Yield of the desired reaction product can be increased by varying the ratio of the reaction precursor carboxylic acids.

1. Catalyst Preparation

To improve the selectivity in the reaction of carboxylic acid mixtures to form ketones, it is necessary to prepare a chemically structurally-regulated inorganic polymer catalyst containing at least two metal oxides—$ThO_2$ and a second metal oxide. The two-metal inorganic polymer catalyst generally takes the following structure where M is the metal from the second metal oxide:

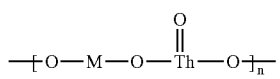

A two-metal inorganic polymer catalyst as described herein has broad application in the creation of ketones from different classes of carboxylic acid mixtures. This catalytic system can be used for the preparation of various ketones, particularly alkyl-aromatic ketones. Application of this catalytic system can sharply decrease the occurrence of byproducts and increase the yield of the desired ketone or reaction product. In the case of the production of MBK from acetic and phenylacetic acids, this means that application of the two-metal inorganic polymer catalyst leads to a reduction in the production of the acetone and di-benzyl-ketone byproducts and an increase in the production of the desired MBK.

To create the two-metal inorganic polymer catalyst, $ThO_2$ and the second metal oxide are sewn to the surface of an inert substrate. Metal oxides including but not limited to cobalt, magnesium, nickel, manganese, and aluminum oxides can be used in this system as the second metal oxide to create the two-metal inorganic polymer catalyst. An example of specific metal oxides that can be used as the second metal oxide are manganese oxides, particularly MnO. With respect to the substrate, there are many different substrates known in the art that can be used, including but not limited to $SiO_2$, $TiO_2$, $ZrO_2$, MgO, and pumice.

In one specific embodiment, pumice is used as the substrate and MnO is the second metal oxide. When pumice is used as the substrate, small-sized pieces of substrate, preferably pea-sized, are treated for about 4 hours with hot, concentrated nitric acid and then washed with hot distilled water until the pH equals about pH 7. The pumice is then mixed with a solution of thorium nitrate in water ($Th(NO_3)_4 \cdot 12H_2O$). The thorium nitrate/water solution can, for example, be comprised of 53 g of thorium nitrate in 95 ml water. The solution is evaporated dry with frequent or continuous stirring to ensure even distribution of the salt. The soaked pumice is then heated in a furnace until some or all of the nitrate breaks down.

A solvent such as diethyl ether or di-isobuthyl is then added to the prepared pumice and carefully mixed. Powder-like MnO is added evenly to the solvent-$ThO_2$-pumice system and mixed. The $ThO_2$ and MnO can be used in a range of mole ratios from about 6:1 to about 12:1, preferably in an approximately 9:1 mole ratio correlation. For the above mentioned amount of thorium-nitrate/water solution, 50 g of MnO is preferred. This mixture is mixed for about 2 hours. The ether is then evaporated. The dry catalyst consists of pumice on the surface of which $ThO_2$ and MnO have been added.

In a second specific example, the catalyst can be prepared by treating pea-sized purified pumice with a solution containing equivalent quantities of $Th(NO_3)_4$ and $Mn(NO_3)_2$ in water.

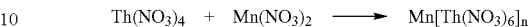

After treating pumice with the double salt solution, the pumice is dried. The pumice is placed in a furnace and heated at approximately 650° C. until the $NO_2$ has been removed. The inorganic polymer formed in and on the surface of the pumice has the regular structure shown in the following reaction:

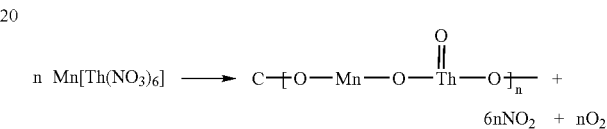

2. Ketone Preparation Process

The two-metal inorganic polymer catalyst described is useful for producing ketones. In one example using the two-metal inorganic polymer catalyst described above, catalytic decomposition of acetic and phenylacetic acids proceeds by the following scheme to form MBK:

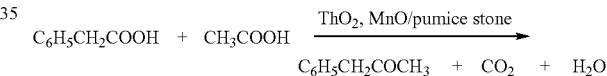

Referring to FIG. 1, the catalytic decomposition of a mixture of acetic and phenylacetic acids is carried out in a reactor 13. A middle-portion of the reactor 13 is filled with a catalyst. A furnace 12 is used for heating the reactor 13 and preferably the middle-portion of the reactor containing the catalyst. The race 12 and/or the reactor 13 will usually have temperature regulation system 18. When the second metal oxide is MnO, the reactor is heated to about 430° C. to about 470° C., preferably about 430° C. to about 460° C., more preferably to about 455° C. Carbon dioxide is added to the reactor 13 from a $CO_2$ gas cylinder 14. The $CO_2$ is preliminarily passed through a $CO_2$ flowmeter 19 and then through a washing bottle 15 that contains concentrated sulfuric acid. The flowmeter 19 and the washing bottle 15 are useful for determining of gas passage rate and for purifying the $CO_2$. After passing through the washing bottle 15, $CO_2$ enters and passes through the catalytic reactor 13.

A mixture of phenylacetic acid and glacial (ice) acetic acid is placed into a mixing vessel 11. The mixture can be comprised of phenylacetic acid and acetic acid in mole ratios in the range of about 1:2 to about 1:4, preferably about 1:2. To increase the yield of MBK, it is necessary to increase the amount of acetic acid. Increasing the phenylacetic acid in the mixture tends to increase the undesirable formation of the di-benzyl-ketone by-product. Therefore, the addition of twice as much acetic acid helps direct the reaction to form the desired MBK product. A good mole ratio is 1:2 as this ratio provides a high MBK yield and is economically acceptable.

After mixing, the mixture is transferred from the mixing vessel 11 into the reactor 13, which is heated by the furnace 12.

After the mixture passes through the reactor 13, it can be cooled by a cooling system 16 utilizing a coolant 20. A fluorescing light-brown oily liquid layer and a water layer are accumulated in a collector 17. The resulting $CO_2$ 21 is allowed to exit the collector 17. Both layers are treated with a mixture of ice and water and are then alkalized to pH of about 7.5 to about 8.5, preferably with a sodium hydroxide or a potassium-hydroxide solution, more preferably with a sodium-hydroxide solution. The oily layer is separated from the water layer. The water layer is then extracted with benzene. The benzene extracts are collected and combined with the oily layer. The benzene is then distilled off. After the distillation in vacuum, MBK yield from this process is generally 70% or greater. Di-benzyl-ketone is produced as a byproduct with a yield of only 5% and is separated from the residue.

In a second specific embodiment, $Al_2O_3$ is used as the second metal oxide. In this embodiment, the reactor 13 temperature range is preferably about 400° C. to about 450° C.

3. Experiments

In one experiment, the reactor 13 is made of refractory pipe 83 cm in length and 18 mm in diameter. The middle of the reactor 13, approximately 56 cm thereof, is filled with the two-metal inorganic polymer catalyst.

A mixture of 130 g of phenylacetic acid with a melting point of 72-76° C. and 112 g of glacial acetic acid is placed into a mixing vessel 11. After mixing, this mixture is transferred into the reactor 13 which is heated by a furnace 12. The mixture is transferred from the mixing vessel 11 to the reactor 13 over a period of about 50 minutes.

After the mixture passes through the reactor 13, a fluorescing light-brown oily liquid and a water layer are accumulated in the collector 17. Both layers are treated with a 250 g mixture of ice and water and are then alkalized to a pH of about 7.5 to about 8.5 with a 50% sodium-hydroxide solution. The oily layer is separated from the water layer. The water layer is then extracted with 50 ml of benzene. The benzene extracts are collected with the oily layer. The benzene is then distilled off. After the distillation in vacuum, 98 g of MBK remains, boiling at 110-120° C. in 21-22 mm Hg. MBK yield from this process is 76.5%.

Test 2. According to above described method and example, 45 g of MBK is prepared from a mixture containing 65 g phenylacetic and 56 g glacial (ice) acetic acids. The yield is 11%.

Test 3. According to above described method and example, 134.5 g of MBK is prepared from a mixture containing 195 g phenylacetic and 168 g glacial (ice) acetic acids. The yield is 70%.

All references cited herein are incorporated by reference to the maximum extent allowable by law. To the extent a reference may not be fully incorporated herein, it is incorporated by reference for background purposes and is indicative of the knowledge of one of ordinary skill in the art.

The embodiments disclosed herein have been described in sufficient detail to enable those skilled in the art to practice the principles of the present invention, and it is understood that other embodiments may be utilized and that logical chemical, mechanical, and process changes may be made without departing from the spirit or scope of the principles of the present invention. To avoid detail not necessary to enable those skilled in the art to practice the principles of the present invention, the description may have omitted certain information known to those skilled in the art.

It should be apparent from the foregoing that an invention having significant advantages has been provided. Although the principles of the present invention have been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiments and examples disclosed might be readily utilized as a basis for modifying or designing other structures for carrying out the same purposes of the principles of the present invention. It should also be realized by those skilled in the art that such equivalent constructions do not depart from the spirit and scope of the principles of the present invention as set forth in the appended claims.

The forgoing detailed description is, therefore, not to be taken in a limiting sense, and the scope of the present invention is defined only by the appended claims. It is therefore contemplated that the claims will cover any such modifications or embodiment that fall within the true scope of the principles of the present invention.

What is claimed is:

1. A process for producing methyl-benzyl-ketone comprising:
    combining phenylacetic acid and acetic acid to form a reaction mixture;
    reacting the reaction mixture in a reactor containing an inorganic polymer catalyst comprised of thorium dioxide and manganic oxide on a pumice substrate; and
    extracting the resulting methyl-benzyl-ketone.

2. A process for producing methyl-benzylketone (MBK) with high yield and purity comprising:
    combining acetic acid, phenylacetic acid, dry carbon dioxide and a catalyst, having a repeating structure —O—M—O—Th—O— on pumice, wherein M is a second metal.

3. The process of claim 2, wherein the second metal is selected from the group consisting of manganese, cobalt, magnesium, aluminum, and nickel.

4. The process according to claim 2 wherein:
    the second metal oxide comprises MnO.

5. The process according to claim 2 wherein:
    the acetic acid and the phenylacetic acid are combined based on a specific mole ratio and
    the specific mole ratio of the acetic acid to the phenylacetic acid being in the range of about 2:1 to about 4:1.

6. The process according to claim 5 wherein:
    the mole ratio of the acetic acid to the phenylacetic acid is about 1:2.

7. The process according to claim 2 further comprising:
    reacting the combined acetic acid and phenylacetic acid in a reactor containing inorganic polymer catalyst on pumice; and
    heating the reactor to a temperature between about 430 to about 470° C. to form a reaction product.

8. The process according to claim 7 wherein:
    the temperature is in a range of about 455 to 465° C.

9. The process according to claim 7 further comprising:
    gathering the reaction product which comprises a first organic layer and a second water layer,
    washing the reaction product with $H_2O$;
    neutralizing the reaction product with alkaline; and
    extracting the methyl-benzyl-ketone.

10. The process according to claim 9 wherein extracting further comprises:

extracting the water layer with benzene to prepare a benzene extract;
  combining the benzene extract with the organic layer;
  distilling off the benzene; and
  separating the resulting methyl-benzyl-ketone from any byproducts.

* * * * *